(12) United States Patent
Rensen et al.

(10) Patent No.: US 9,895,064 B2
(45) Date of Patent: Feb. 20, 2018

(54) DEVICE AND METHOD FOR DETERMINING A DISEASE ACTIVITY

(75) Inventors: Wouter Harry Jacinth Rensen, Eindhoven (NL); Pieter Klaas De Bokx, Eindhoven (NL)

(73) Assignee: Hemics B.V., Eindhoven (NL)

( * ) Notice: Subject to any disclaimer, the term of this patent is extended or adjusted under 35 U.S.C. 154(b) by 68 days.

(21) Appl. No.: 13/989,800

(22) PCT Filed: Nov. 25, 2011

(86) PCT No.: PCT/EP2011/071043
§ 371 (c)(1),
(2), (4) Date: Aug. 2, 2013

(87) PCT Pub. No.: WO2012/069637
PCT Pub. Date: May 31, 2012

(65) Prior Publication Data
US 2013/0310697 A1    Nov. 21, 2013

(30) Foreign Application Priority Data
Nov. 26, 2010    (EP) .................................... 10192684

(51) Int. Cl.
*A61B 5/05*    (2006.01)
*A61B 5/00*    (2006.01)
*A61B 5/026*    (2006.01)
*A61B 5/022*    (2006.01)

(52) U.S. Cl.
CPC .......... *A61B 5/0082* (2013.01); *A61B 5/0075* (2013.01); *A61B 5/4528* (2013.01); *A61B 5/4842* (2013.01); *A61B 5/022* (2013.01); *A61B 5/0261* (2013.01); *A61B 5/6825* (2013.01); *A61B 5/6829* (2013.01)

(58) Field of Classification Search
CPC ........................... A61B 5/0075; A61B 5/0082
See application file for complete search history.

(56) References Cited

U.S. PATENT DOCUMENTS

| | | | |
|---|---|---|---|
| 6,172,743 B1 * | 1/2001 | Kley et al. ...................... | 356/39 |
| 2002/0007121 A1 * | 1/2002 | Jackson et al. ................ | 600/475 |
| 2007/0078308 A1 * | 4/2007 | Daly ....................... | A61B 3/117 |
| | | | 600/310 |
| 2011/0066034 A1 * | 3/2011 | Rensen et al. ................. | 600/473 |
| 2012/0316421 A1 * | 12/2012 | Kumar et al. ................. | 600/407 |

FOREIGN PATENT DOCUMENTS

| | | |
|---|---|---|
| WO | 2009/022003 A1 | 2/2009 |
| WO | 2009/147560 A2 | 12/2009 |
| WO | 2010/064202 A2 | 9/2010 |

\* cited by examiner

*Primary Examiner* — Jonathan Cwern
(74) *Attorney, Agent, or Firm* — Saile Ackerman LLC; Stephen B. Ackerman; Rosemary L.S. Pike

(57) ABSTRACT

A system and method to determine a disease activity as a single value by way of optical measurements in order to facilitate an analysis of a current disease status and a future course of disease, thus assisting a doctor's diagnosis or decision on a therapy. A blood perfusion is varied in an area of interest, the area of interest is irradiated with light of at least two wavelengths, an intensity of light reflected and/or transmitted by the area of interest is detected, features are derived from detected intensity curves of at least two predetermined wavelengths under at least two different perfusion conditions, and the disease activity is determined using these features.

18 Claims, 8 Drawing Sheets

DEVICE AND METHOD FOR DETERMINING A DISEASE ACTIVITY

CROSS-REFERENCE TO RELATED APPLICATIONS

The present application is a National Stage Application of PCT International Application No. PCT/EP2011/071043 (filed on Nov. 25, 2011), under 35 U.S.C. § 371, which claims priority to European Patent Application No. 10192684.8 (filed on Nov. 26, 2010), which are each hereby incorporated by reference in their respective entireties/

TECHNICAL FIELD

The invention relates to a system and a method for determining a disease activity, and in particular to a system and a method for determining a disease activity by means of optical measurements.

BACKGROUND

Rheumatoid arthritis (RA) is one of the most frequent chronic rheumatic diseases affecting large parts of the population. This autoimmune disease causes chronic inflammation of joints, which destroys the joints in the course of time and limits their flexibility.

In general, the treatment of rheumatoid arthritis is staged. First, a patient receives painkillers, which are frequently followed by non-steroid anti-inflammatory drugs (NSAIDs) and disease modifying anti-rheumatic drugs (DMARDs). The last stage of the medical treatment is the use of biological therapies or immune therapies, in order to reduce the ability of the body's immune system to start or maintain unnecessary joint inflammations. As a last measure, operative treatments are performed, resulting in the extreme in artificial joints or operative stiffening of the concerned joints. Especially the immune therapies and operative treatments are very expensive and may cost tens of thousands of dollars per year and patient. Furthermore, drugs used in later stages of treatment can also go along with severe side effects. Since rheumatoid arthritis is a progressive disease, early diagnosis and start of treatment can help postponing adverse effects and high costs of treatment. For deciding on a therapy for a patient, doctors consider a disease activity, e.g. the number and severity of inflamed joints. Thus, a meaningful and intuitive measure of disease activity will help to simplify and accelerate analysis and decision processes for determining an appropriate therapy. Different definitions of disease activity exist for rheumatoid arthritis, most of which are composite indices, such as DAS28, the Health Assessment Questionnaire and others. In the scope of this invention, joint inflammation levels are an important indicator of disease activity.

In rheumatoid arthritis and in many other inflammatory or cancerous diseases, the number and properties of blood vessels in the affected body part are changed, leading to a different perfusion or perfusion dynamics, e.g. in diseased joints. This has been demonstrated, for instance, using time dependent measurements of non-targeted fluorescent dies or other contrast agents. However, in the clinical practice of rheumatologists and other doctors, administration of contrast agents is unfeasible. Moreover, contrast agents are expensive and may be harmful to health or result in immunological reactions.

WO 2010/064202 A2 relates to a device and a method for optical detection of a condition of a joint. An attenuation of light is locally detected for two distinct positions, whereof at least one is the joint to be investigated. Here, the signal resulting from blood can be separated from signals resulting from other sources of light attenuation due to the periodic intensity variations caused by pressure pulses of the patient's blood flow. Since inflamed joints will have a different perfusion and oxygenation compared to healthy joints, the dynamic spectrum behavior will be different.

However, a medical professional has no time for time-consuming analysis of the measured spectra. In particular, although spectra of joints contain information on disease activity, the level of activity is not directly obvious from the measured spectrum. Instead, a medical professional needs an unambiguous and quantitative measure indicating the disease activity as a single value, so that he can make a diagnosis based on the disease activity.

SUMMARY

In view of above disadvantages and problems in the prior art, it is an object of the present invention to provide a system and a method for determining a disease activity as a single value by means of optical measurements in order to facilitate an analysis of a current disease status and/or a future course of disease, thus assisting a doctor's diagnosis or decision on a therapy.

The object is solved by the features of the independent claims.

The invention is based on the idea that a disease activity is related to a perfusion dynamics of an affected body part, e.g. a joint, and can be assessed by means of optical measurements, during which the perfusion of the body part is modified. From the obtained data, features are extracted and combined such that a disease activity can be determined as a single value or a scalar value. Thus, a quantitative measure can be easily and automatically provided for estimating a level of disease, which a medical professional may consider for making a diagnosis.

A first aspect of the invention provides a system for determining a disease activity with respect to an area of interest, comprising a control unit adapted to derive features from detected intensities of light under at least two different perfusion conditions in an area of interest and to determine the disease activity using these features. The detected intensities of light measured under at least two different perfusion conditions may be correlated with disease activities by means of the derived features. The intensities of light may relate to light that is reflected and/or transmitted by the area of interest.

The control unit may be adapted to derive the features from the detected intensities of at least one predetermined wavelength or at least two predetermined wavelengths.

The system may comprise a perfusion manipulation means for varying a blood perfusion in an area of interest; an irradiation unit capable of irradiating the area of interest with light; and a detection unit capable of detecting an intensity of light reflected and/or transmitted by the area of interest.

This allows to perform image or data acquisition to provide the data for the control unit.

The irradiation unit may be capable of irradiating the area of interest with light of at least one wavelength or at least two wavelengths. Using two wavelengths may improve the accuracy.

According to one aspect of the present invention, a system for determining a disease activity is provided comprising a perfusion manipulation means, e.g. a pressure cuff, for varying the perfusion in an area of interest or body part. For performing the optical measurements, an irradiation unit is provided for irradiating the area of interest with light of at least two different wavelengths, so that the local perfusion dynamics can be observed by means of optical measurements. The irradiation unit may be capable of emitting light at different wavelengths simultaneously, e.g. as multi-color or white light, or sequentially, i.e. as one wavelength at a time. Furthermore, the system comprises a detection unit in order to determine an attenuation of light, i.e. an intensity of light reflected and/or transmitted by the area of interest. A control unit can then extract parameters or features from a graph of transmission and/or reflection intensity plotted versus time relating to at least two different perfusion conditions for at least two predetermined wavelengths. Here, the wavelengths emitted by the irradiation unit and/or the wavelengths detected by the detection unit may comprise the predetermined wavelengths used for feature extraction. With the extracted features, the control unit can determine the disease activity. For this, the control unit preferably combines the derived features based on a predetermined algorithm, for instance by performing mathematical operations.

In a further embodiment, the blood perfusion in the area of interest is varied periodically or cyclically by the perfusion manipulation means. The blood perfusion may be varied by retaining blood in the area of interest for a predetermined time and then releasing the blood. Therefore, the perfusion conditions may relate to a case of maximally retained blood and of unobstructed flowing blood, resulting in maximum and minimum attenuation. In case of periodical perfusion manipulation, when choosing two different points in time within one perfusion manipulation cycle, two different perfusion conditions are selected. With a periodical variation, the detected intensity curves can be easier analyzed.

In one embodiment, the irradiation unit can irradiate the area of interest with white or multi-color light. For this, the irradiation unit may comprise any light source having a wide spectral range. In this case, the wavelength selection needs to be performed at the detector side, e.g. by using an optical filter in front of the detection unit or by splitting the reflected and/or transmitted light in several components using dichroic elements or gratings together with multiple detector elements.

In an alternative preferred embodiment, however, the irradiation unit is capable of selecting different wavelengths. Thus, the light emission of the irradiation unit may be switchable for sequentially irradiating the area of interest with one wavelength at a time. If monochromatic light is used for irradiation, i.e. if the wavelength selection is performed at the irradiation side, a broadband detector may be used. In this case, the irradiation unit may comprise a plurality of monochromatic light sources, such as lasers or LEDs, whereas the broadband detector can be realized as any detector with a wide spectral sensitivity, e.g. a CCD or a photodiode. This embodiment is preferred with respect to data quality, set-up geometry and costs. In particular, no expensive and complicated wavelength selection is required at the detection side.

Preferably, the at least two predetermined wavelengths, at which features are extracted and processed for determination of disease activity, correspond to wavelengths that have been illustrated to be the most significant wavelengths for determining disease activity. Thus, the optical measurements may be performed only at these wavelengths, so that examination time is saved and data amount to be analyzed is reduced compared to measurements performed at all available wavelengths. Moreover, when using only a few significant wavelengths for the optical measurements, also system costs can be reduced, since then, fewer components are required. The significance of the wavelengths may depend on the disease to be examined or on particular areas of interests, i.e. body parts, involved in the disease to be examined.

In one embodiment, the predetermined wavelengths used for feature extraction are in the near-infrared or infrared range. For instance, the predetermined wavelengths for analysis, and thus usually also the wavelengths for irradiation, may include six wavelengths at about $586\pm10$ nm, $638\pm10$ nm, $666\pm10$ nm, $808\pm10$ nm, $835\pm10$ nm and $864\pm10$ nm. In a compacter embodiment, the predetermined wavelengths for analysis and/or the wavelengths for irradiation may include four wavelengths at about $666\pm10$ nm, $808\pm10$ nm, $835\pm10$ nm and $864\pm10$ nm. In a preferred embodiment, the predetermined wavelengths for analysis and/or the wavelengths for irradiation may include two wavelengths at about $666\pm10$ nm and $808\pm10$ nm. Therefore, exemplarily referring to the last embodiment, the feature extraction is preferably performed on intensity curves recorded for these wavelengths, e.g. $666\pm10$ nm and/or $808\pm10$ nm. However, the predetermined wavelengths for feature extraction and/or the predetermined algorithm for deriving the disease activity from the extracted features may be chosen according to a disease to be evaluated, which can in general be any disease affecting the perfusion of a body part of a patient.

In order to assess the disease activity, the control unit may use a predetermined function, in which the derived features are input. The function may be determined by means of regression analysis, linear discriminant analysis, analysis of variants or partial-least-square-discriminant-analysis or the like, e.g. on data of a clinical study. Additionally or alternatively, a regression vector may thus be determined and used for determining the disease activity. The regression vector may comprise weighting coefficients for weighting the different features according to their reliability or influence on the correct determination of the disease activity. In addition, the regression vector may comprise weighting coefficients for patient, environmental and/or calibration parameters, which may be included in the feature vector. These parameters may relate, for instance, to weight or age of the patient, room temperature, or the like. Preferably, the disease activity is determined by taking an inner product of the regression vector and a feature vector comprising the derived features for the predetermined wavelengths and for different perfusion conditions. In this case, the feature vector may correspond to a column vector having a number of rows equal to the product of the number of predetermined wavelengths and the number of the perfusion conditions.

In a preferred embodiment, the system may be adapted to determine a suitable wavelength for irradiation and/or feature extraction. For this, the control unit may be adapted to determine at least one regression vector, so that the regression vector allows relating optical data to a single value indicative for a disease activity at a plurality of different wavelengths. The optical data may be obtained for a group of patients displaying different disease activities, wherein the disease activities are determined also by conventional methods. The regression vector may be determined by means of regression analysis, linear discriminant analysis, analysis of variants or partial-least-square-discriminant-analysis or the like, such that an inner product of the regression vector and a feature vector comprising features derived from optical data of a patient approaches the conventionally determined disease activity of the patient. The most significant and reliable wavelengths are then selected by selecting the wavelengths corresponding to an extremum in the spectrum of the regression vector, wherein the determined regression vector is plotted against the different wavelengths. These wavelengths are used for irradiation as well as for data analysis in future patient examinations. Moreover, the determined regression vector may be used for determining the disease activity, as described above.

In a further preferred embodiment, the control unit determines the disease activity by using the expression:

Disease activity=−1.32×(normalized transmission intensity at an irradiation wavelength of ca. 666±10 nm at a first time point t1)−27.2×(normalized transmission intensity at an irradiation wavelength of ca. 808±10 nm at the first time point t1)+5.98×(normalized transmission intensity at an irradiation wavelength of ca. 666±10 nm at a second time point t2)−23.8×(normalized transmission intensity at an irradiation wavelength of ca. 808±10 nm at the second time point t2), with t1 and t2 being different points in time. That is, in case of a periodic variation of perfusion, t1 and t2 correspond to different perfusion conditions A and B. For instance, when using a pressure cuff as a perfusion manipulation means, condition A may relate to a first time point t1 before cuff inflation and condition B may relate to a second time point t2 after cuff inflation. In this case, the condition A and B thus relate to unobstructed blood flow and obstructed blood flow, respectively. The above expression may be considered as an inner product of a predetermined regression vector comprising the weighting coefficients (−1.32, −27.2, 5.98, −23.8) and a feature vector comprising the detected intensities at ca. 666±10 nm and 808 nm at two different time points t1 and t2, respectively. The weighting coefficients of this expression may have been determined by applying regression analysis or discriminant analysis to a data set of a clinical study for the wavelengths of about 666±10 nm and about 808±10 nm.

As features used for determining the disease activity, a maximum intensity, a minimum intensity, an intensity amplitude or intensity difference, a drift, a drop time, an inflection point, any other parameter determined by mathematical operations or any combination thereof may be derived from the intensity curves. Alternatively or additionally, fit parameters obtained by fitting the measured intensity curves or parts thereof may be used for determining the disease activity.

The disease activity may relate to an inflammation level for indicating a status of an inflammatory disease, e.g. the disease activity of rheumatoid arthritis (RA). However, the system may also be used for determining the disease activity for other diseases, which affect the blood perfusion of a body part or area of interest, such as cancer, wherein the blood perfusion is changed around tumors. In this case, a predetermined wavelength for feature extraction may be chosen according to the disease or according to the body part under investigation. Here, the physiological components of different body parts may be considered, resulting in different optical properties. Moreover, when a regression vector is used, also the regression vector may be chosen depending on the disease or affected body part. When the disease activity relates to rheumatoid arthritis, the area of interest or body part to be investigated is preferably a joint, and in particular, a joint of the hand or foot.

In a further preferred embodiment, optical measurements are performed at different positions of a patient's body, e.g. on different joints. By these means, an overall disease status may be determined for the patient. Moreover, a reference area may be chosen for calibrating the measurements. Thus, particular properties of the patient may be considered, such as a thickness of absorbing layers e.g. fat, or a diameter of joints.

In a further aspect of the present invention, a method for determining a disease activity with respect to an area of interest is provided. The method comprises the steps of: deriving features from detected intensities of light under at least two different perfusion conditions in an area of interest; and determining the disease activity using these features.

The step of deriving features from detected intensities may comprise deriving the features from the detected intensities of at least one predetermined wavelength or at least two predetermined wavelengths.

The method may comprise varying a blood perfusion in the area of interest; irradiating the area of interest with light; and detecting an intensity of light reflected and/or transmitted by the area of interest.

The irradiating the area of interest with light may comprise irradiating the area of interest with light of at least two wavelengths.

In a further aspect of the present invention, a method for determining a disease activity is provided. In this method, a blood perfusion is varied in an area of interest, while the area of interest is irradiated with light of at least two wavelengths. An intensity of reflected and/or transmitted light is detected and features are derived from the detected intensity curves under at least two different perfusion conditions. For the feature extraction, intensity curves of predetermined wavelengths are selected. These predetermined wavelengths preferably relate to the most significant wavelengths for reliably determining a disease activity. The derived features are used for determining the disease activity. For instance, the features can be combined using a predetermined algorithm, so that the disease activity is obtained therefrom as a single value. By these means, a single value indicating the severity of the disease is provided to a doctor, so that he can easily decide on further therapies.

In a further aspect of the invention, a computer program product is provided for causing a processor system to perform the steps of deriving features from detected intensities of light under at least two different perfusion conditions in an area of interest; and determining the disease activity using these features.

DRAWINGS

DESCRIPTION

Figure 1:
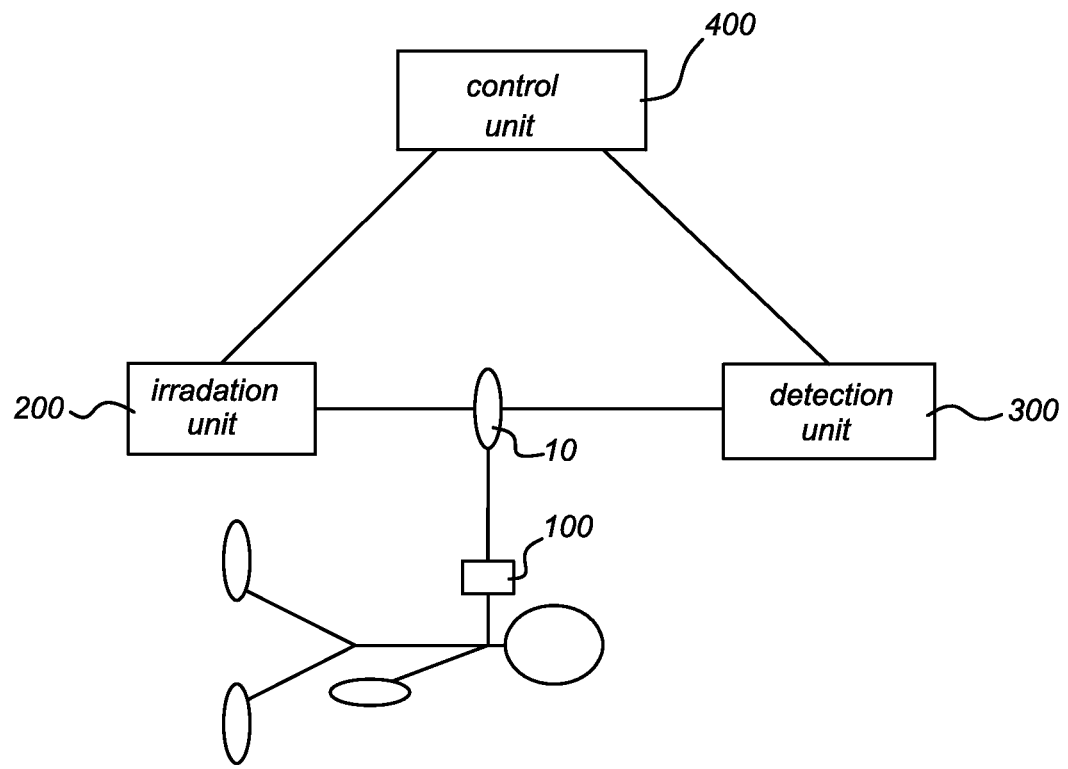
FIG. 1 illustrates a system for determining a disease activity according to the present invention.

In FIG. 1, a system according to the present invention is illustrated. The system comprises an irradiation unit 200, a detection unit 300 and a control unit 400. In one embodiment, the irradiation unit 200 comprises at least one or at least two monochromatic light sources for emitting light at a desired wavelength or at desired wavelengths, as for example LEDs or laser diodes. The light at the desired wavelength or wavelengths is irradiated to a body part or area of interest 10 of a patient and the transmitted light is detected by the detection unit 300. Possibly, a matching medium is used for optically coupling the area of interest 10 with the irradiation unit 200 or the detection unit 300. In this embodiment, the detection unit 300 can comprise a broadband detector e.g. a CCD or a photodiode. The detected signals are provided to the control unit 400 in order to be processed and analyzed. The control unit 400 may also control the irradiation unit 200 or the detection unit 300.

For example, the irradiation unit 200 comprises one monochromatic light source for emitting light at a desired wavelength. This wavelength can be chosen to match a spectral absorption characteristic of the body part or area of interest. In another example, the irradiation unit 200 comprises at least two monochomatic light sources for emitting light at desired wavelengths, where these wavelengths can be chosen to match different spectral absorption characteristics of the body part or area of interest, which may improve the amount of information available from the measured signals. Features described herein in respect of a system based on at least two wavelengths of light may similarly be applied to a system based on one wavelength of light.

In an alternative embodiment, the irradiation unit 200 comprises a broadband light source emitting white light. In this embodiment, the detection unit 300 is adapted to differentiate between different wavelengths, e.g. by using an optical filter, such as a multilayer dielectric filter, an absorption filter, an acoustic-optical filter etc. Alternatively, the transmitted light can be split into several components according to the different wavelengths by using dichroic elements or gratings in combination with multiple detector elements. In a further alternative embodiment, the system may be operated in reflection mode, i.e. reflected light is detected. Here, the detection unit 300 and the irradiation unit 200 can be combined.

In the following, however, a system according to the first embodiment is described, which is operated in transmission mode and comprises an irradiation unit 200 capable of emitting monochromatic light at different wavelengths, yet without being limited thereto. Thus, the other mentioned embodiments for a system can be employed in a similar way. Moreover, it is referred in the following to determining a disease activity of rheumatoid arthritis. Thus, the investigated area of interest 10 relates to joints, e.g. to finger joints. However, the present invention may also be applicable to other diseases affecting the perfusion of any body area.

During examination of a patient, a doctor selects one or more specific wavelengths for irradiating the area of interest 10, e.g. 666 nm and 808 nm. The transmitted light is detected by the detection unit 300 and the resulting intensity curve is recorded for the specific wavelengths over time. During the optical measurement, blood perfusion can be varied in the irradiated area of interest 10 using a perfusion manipulation means 100, such as a pressure cuff. When the perfusion manipulation means 100 is operated, the blood is pooled in the area of interest 10, so that the attenuation of transmitted light becomes maximum, i.e. the intensity of transmitted light becomes minimum. Likewise, when the perfusion manipulation means 100 are released, the obstructed blood flows out of the area of interest 10, so that the attenuation of the transmitted light and the intensity of the transmitted light return to their initial values.

Figure 2:
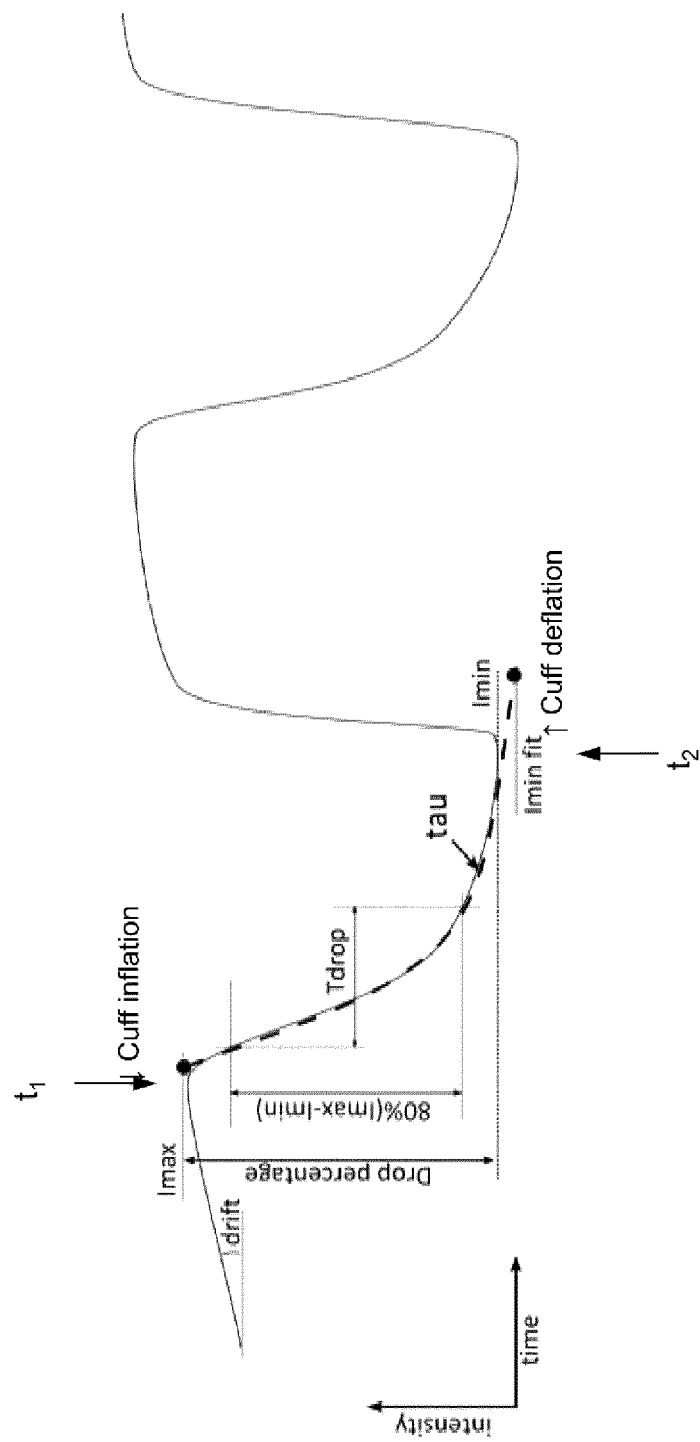
FIG. 2 illustrates an intensity curve obtained when operating the system of FIG. 1.

In FIG. 2, an intensity curve I ($\lambda$, t, x) obtained in an optical transmission measurement is illustrated for a particular wavelength $\lambda$ and a particular position x of the area of interest 10. In the optical measurement, the area of interest 10 is irradiated at the selected wavelength $\lambda$ and the intensity transmitted through the area of interest 10 is continuously detected by the detection unit 300. During the optical measurement, the pressure cuff 100 is inflated and deflated (see arrows) at predetermined time points t1 and t2 so as to occlude and release the blood flow. During occlusion, more blood is present in the measured area of interest 10, leading to a decreased transmission of light, i.e. to a lowered intensity Imin. As indicated in FIG. 2, different parameters or features can be extracted from the recorded intensity curve I($\lambda$, t, x). For instance, when the blood is flowing unobstructed, there can nevertheless be a drift in the transmitted intensity. As indicated, the drift may be defined as an angle between a plateau of the intensity curve and a horizontal line. Moreover, the values of maximum or minimum intensity Imax and Imin can be extracted as well as a relative difference between the intensities before inflation and deflation of the pressure cuff 100, i.e. a percentage of drop with respect to the maximum intensity (drop percentage). Furthermore, a drop time Tdrop can be determined, indicating a time interval, in which the intensity drops by a predetermined percentage of the intensity amplitude, e.g. by 80% of the difference between the maximum intensity Imax and the minimum intensity Imin. Additionally, a part of the intensity curve may be fitted by a fit function. Then, fit parameters can be used as features for determining the disease activity, e.g. a Imin_fit, an exponential time constant $\tau$, etc. Examples of features are illustrated in table 1. Similar parameters can be extracted for the intensity curve, when the pressure cuff 100 is deflated, and for a repeated inflation-deflation cycle.

TABLE 1

| Feature (F) | Unit | Description |
| --- | --- | --- |
| Drift | W/s | Unintentional change in intensity with deflated pressure cuff |
| $I_{max}$ | W | Intensity before cuff inflation |
| $I_{min}$ | W | Intensity before cuff deflation |
| Drop percentage | % | Relative difference between $I_{max}$ and $I_{min}$ |
| $T_{drop}$ (80%) | s | Signal drop time for an intensity drop of a certain percentage (e.g. 80% of total drop) |
| Tau | s | Time constant associated with exponential fit to the intensity trace during cuff inflation |
| $I_{min\_fit}$ | W | Asymptotic intensity associated with an exponential fit to the intensity curve during cuff inflation |

Figure 3:
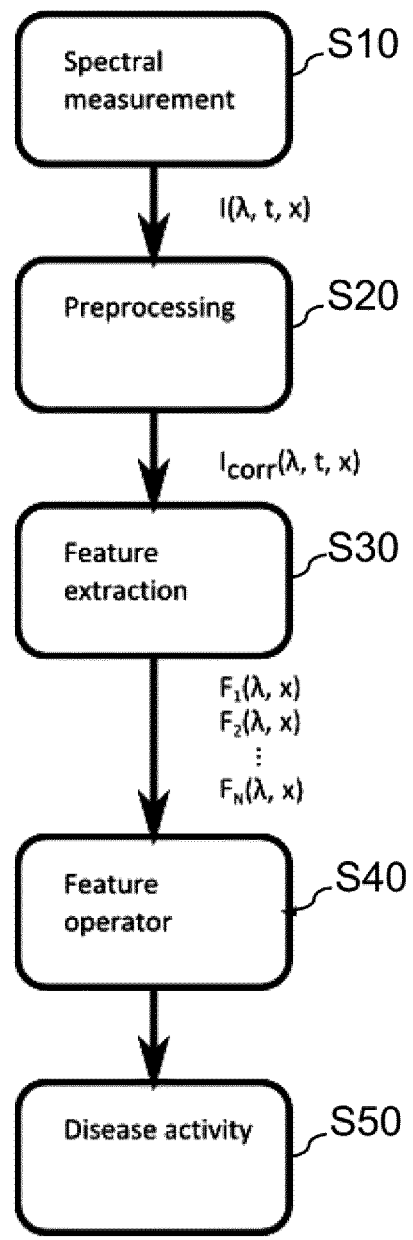
FIG. 3 illustrates a flow diagram for determining a disease activity according to a first embodiment of the present invention.

In FIG. 3, a method for determining a disease activity according to a first embodiment of the present invention is illustrated. After recording the intensity curve I($\lambda$, t, x) for one or more selected wavelengths at one or more areas of interest 10 (S10), the measured intensity curve I($\lambda$, t, x) can be corrected or calibrated in a first data processing step (S20). For instance, light source and other system characteristics that are stored in a memory can be used for calibrating the measured data. Also other processing steps can be performed, e.g. taking derivates, subtracting an offset or average signal, dividing by the standard deviation of the signal or other mathematical operations. Moreover, electronic filtering may be applied to the intensity curve in order to remove noise from the signal. However, in some situations, no preprocessing step (S20) may be required. From the resulting corrected intensity curve $I_{corr}(\lambda, t, x)$, various features or parameters $F_1(\lambda, x), \ldots, F_N(\lambda, x)$ can be derived (S30), as described above. For instance, the extracted features $F_1(\lambda, x) \ldots, F_N(\lambda, x)$ can relate to intensities taken at a specific point in time or under a specific perfusion condition. Steps S10, S20 and S30 are performed for all selected wavelengths $\lambda$. In case of measuring several areas of interest 10, i.e. several joints, these steps S10, S20 and S30 are also repeated for the different positions x. Then, the features $F_1(\lambda, x), \ldots, F_N(\lambda, x)$ are inserted in a function or so-called feature operator (S40) and a disease activity is determined (S50). The disease activity may be quantified on an arbitrary scale, e.g. from 1 to 5 for arthritis, with 1: no inflammation; 2: maybe/slight inflammation; 3: moderate inflammation; 4: inflammation; and 5: severe inflammation. As a first example of a feature operator, expression (1) is illustrated:

$$A_{x1,x2} = C\left(\frac{I_{max,\lambda 1,x1} - I_{min,\lambda 1,x1}}{I_{max,\lambda 2,x1} - I_{min,\lambda 2,x1}} - \frac{I_{max,\lambda 1,x2} - I_{min,\lambda 1,x2}}{I_{max,\lambda 2,x2} - I_{min,\lambda 2,x2}}\right) \quad (1)$$

In this expression (1), A is an inflammation level of position x1 with reference position x2, C is predetermined constant and $I_{max}$ and $I_{min}$ refer to the maximum and minimum intensity, respectively, at the corresponding wavelengths $\lambda_1$ and $\lambda_2$ and positions $x_1$ and $x_2$. Thus, the features $F_1(\lambda, x), \ldots, F_N(\lambda, x)$ derived from the measured intensity curves $I(\lambda, t, x)$ can be used to compose a single value A, relating to a position-dependent inflammation level or disease activity. It should be noted that equation (1) is only an example. Thus, other mathematical operations are also possible. In a modification of this embodiment, the feature operator may include data from multiple positions $x_{1i}$ in order to calculate an average inflammation level $A_{av}$. These positions $x_i$ relate to positions of joints in the measured body part, such as joints in a hand.

Figure 4:
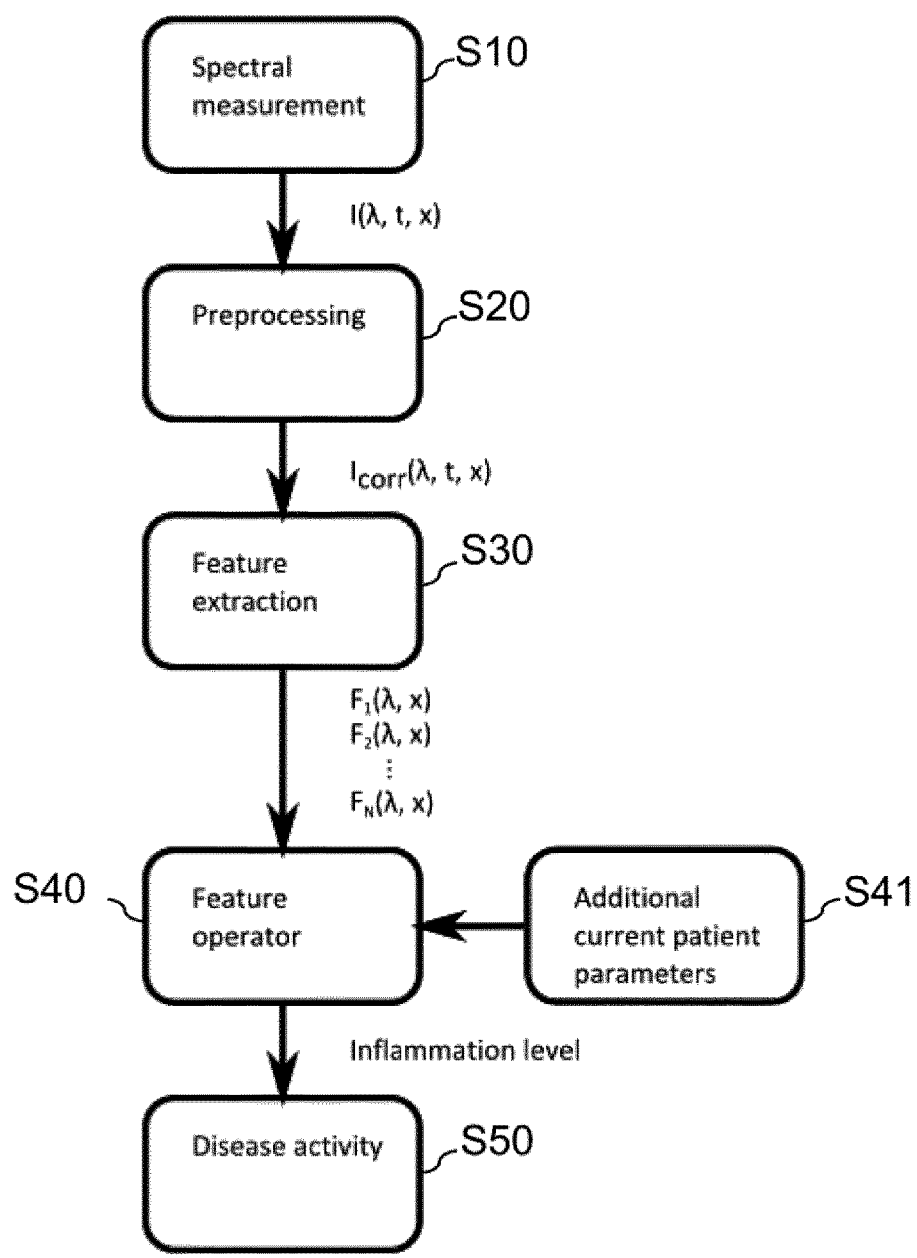
FIG. 4 illustrates a flow diagram for determining a disease activity according to a second embodiment of the present invention.

In FIG. 4, a flow diagram for another method for determining a disease activity of a patient is illustrated. Steps S10-S50 are the same as described for the first embodiment illustrated in FIG. 2. However, in this embodiment, additional patient parameters are measured or determined (S41) and considered in the feature operator (S40). For instance, this can be achieved by include the additional patient parameters in the constant C of expression (1). Alternatively, these parameters may be included as features Fi. For example, the additional patient parameters may refer to a current physiological situation of the patient, e.g. age, gender, body mass index, blood pressure, heart rate or the number or the distribution of inflamed joints. Preferably, these additional patient parameters do not require complicated measurements, as the determination of laboratory values does. Thus, a very simple and accurate method is provided for assessing an inflammation level or a disease activity by means of optical measurements without the need of data acquisition or by means of laboratory values.

Figure 5:
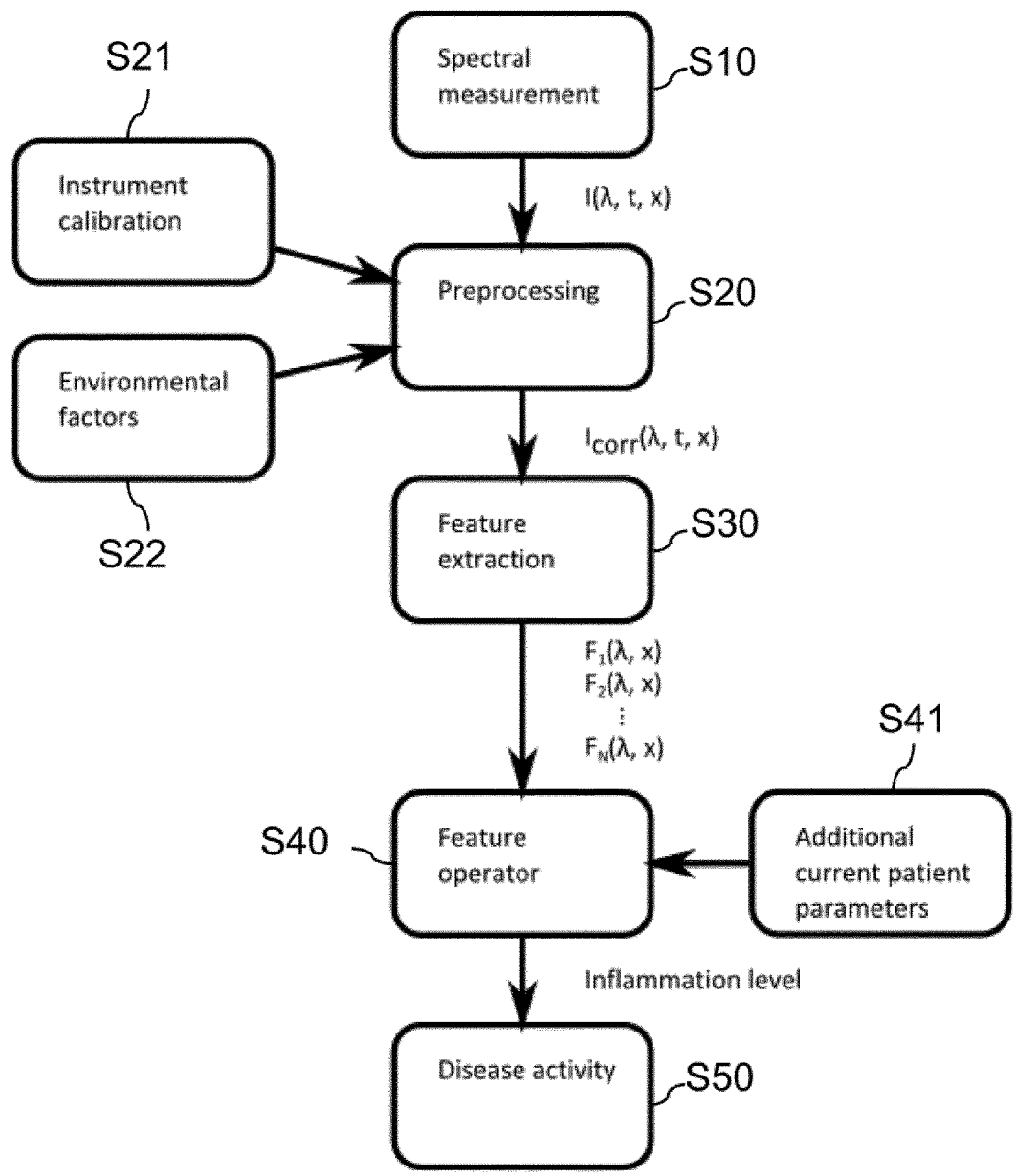
FIG. 5 illustrates a flow diagram for determining a disease activity according to a third embodiment of the present invention.
Figure 6:
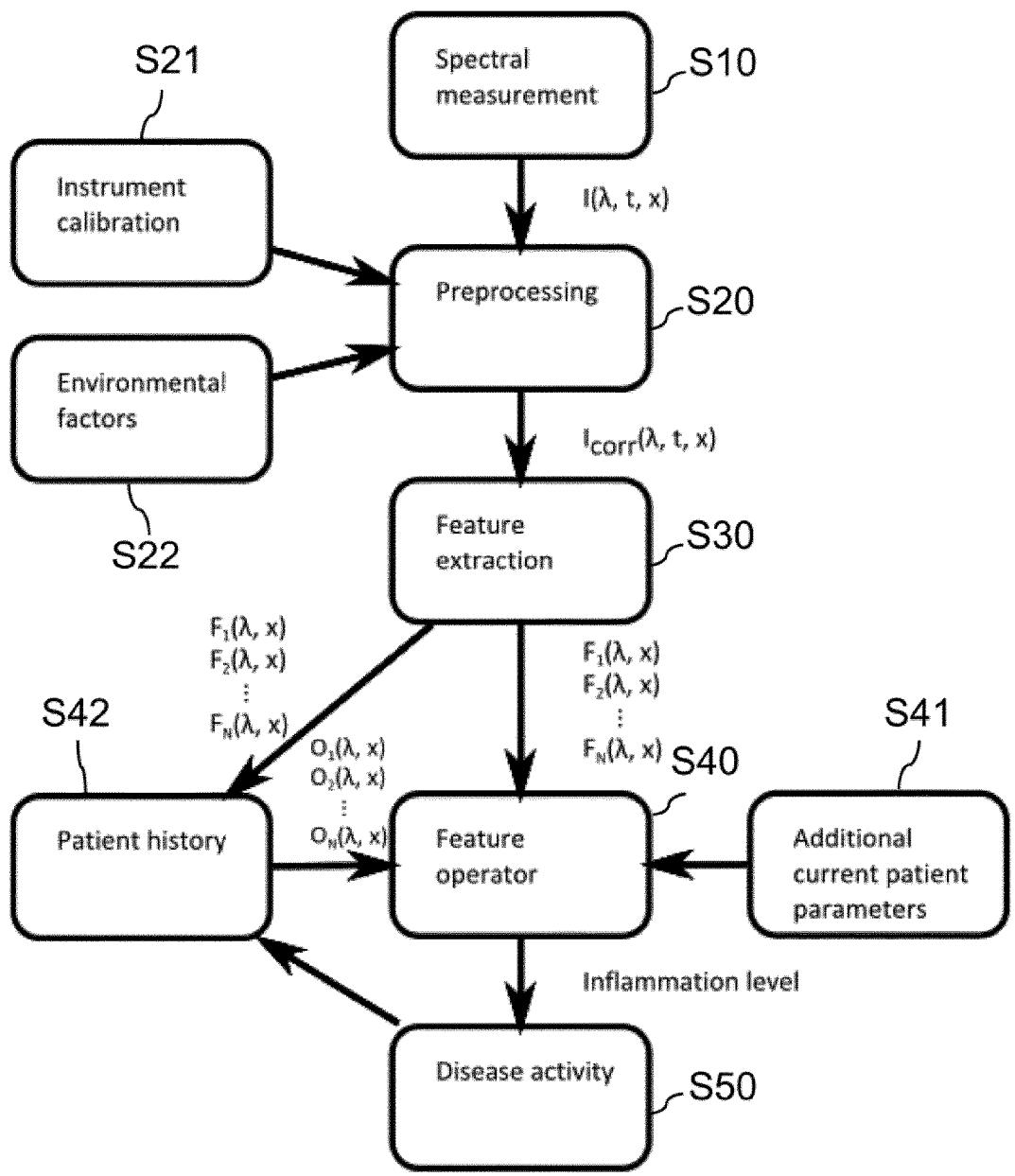
FIG. 6 illustrates a flow diagram for determining a disease activity according to a fourth embodiment of the present invention.

In a further embodiment, as illustrated in FIG. 5, the method may further comprise steps for instrument calibration (S21) and a calibration with respect to environmental factors (S22). The instrument calibration may be an automatic dedicated calibration mode, e.g. for establishing a reference white light spectrum. Here, a phantom is possibly used. By these means, absolute transmission measurements can be achieved. Alternatively or additionally, environmental factors such as room temperature, relative humidity and air pressure may be considered. The instrument calibration parameters as well as the environmental factors may be used in the preprocessing step (S20) before feature extraction (S30). However, it is also possible to adjust the feature operator of step S40 accordingly, e.g. by correcting the constant C of expression (1).

When a patient is treated for a longer time, as it is mostly the case for a chronic disease, a history of the patient may be recorded. In other words, after having extracted features from the measured intensity curves $I(\lambda, t, x)$ (S30), these features $F1(\lambda, x), \ldots, FN(\lambda, x)$ may be stored in a memory. Then, the patient history can be considered in future examinations of the patient, thus considering the development of the disease. Parameters significant for the patient history $O1(\lambda, x), \ldots, ON(\lambda, x)$ may be used in the feature operator (S40), e.g. the historic features may be included in the constant C of expression (1). Thus, actual values may be compared with historic ones. After having derived the disease activity (S50), the disease activity may also be stored in the patient's history. By these means, a disease development is more accurately followed and future course of disease can be more accurately predicted.

Figure 7:
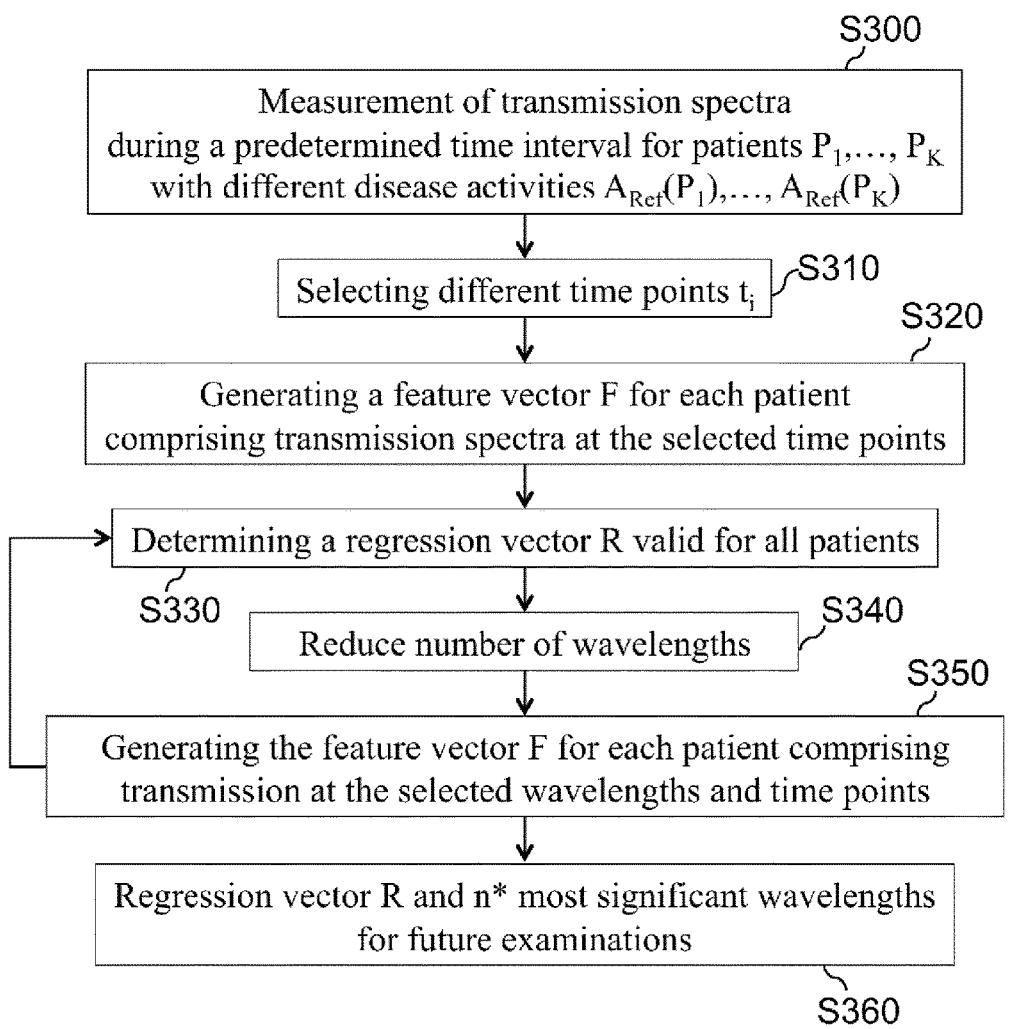
FIG. 7 illustrates a flow diagram for setting-up a system according to the present invention.

In the following, it will be described with reference to FIGS. 7 and 8, how the wavelengths used for irradiation and analysis can be selected for the systems and methods according to the present invention. First, a clinical study is performed. In this clinical study, optical data are collected for a group of patients P1, . . . , PK having different disease activities under the same examination conditions, under which future patient examinations will be performed, e.g. with respect to the measurement geometry. The disease activities of the patients are determined by conventional means as reference disease activities Aref (P1), . . . , Aref (PK) in order to be later compared to the disease activities determined according to the present invention. For instance, the reference disease activities Aref (P1), . . . , Aref (PK) are determined by a doctor using laboratory values or the like. As in the examples described above, transmission spectra are measured for each patient Pi during a predetermined time interval at a plurality of different wavelengths $\lambda 1, \ldots, \lambda n$, while a pressure cuff 100 is periodically inflated and deflated. This results in a 2-dimensional matrix of data for each patient, as illustrated in expression (2):

$$I_{\lambda,t}(P_i) = \begin{pmatrix} I_{\lambda 1,t1} & K & I_{\lambda n,t1} \\ \vdots & & \vdots \\ \vdots & & \vdots \\ \vdots & & \vdots \\ I_{\lambda n,t1} & L & I_{\lambda n,tm} \end{pmatrix} \quad (2)$$

Here, the intensity curves $I(\lambda i)$ for the different wavelengths $\lambda i$ are listed in the respective columns and the different points in time ti correspond to the rows of the matrix. Then, particular time points ti are selected (S310), for instance time points t1 and t2. In the next step S320, a feature vector F(Pi) is determined for each patient Pi, comprising the features derived from the intensity curves at the different wavelengths for the selected time points. As mentioned before, these features may relate to transmission intensities Iλi, ti at the selected points in time. These time points t1 and t2 may relate to a situation just before inflation and just before deflation, respectively. In this case, the corresponding intensities recorded at the point in time just before inflation and just before deflation relate to the maximum and minimum intensity, respectively. The feature vector is a 1-dimensional vector, as illustrated in expression (3):

$$F(P_i) = \begin{pmatrix} F_{\lambda 1, t1} \\ \vdots \\ F_{\lambda n, t1} \\ F_{\lambda 1, t2} \\ \vdots \\ \vdots \\ F_{\lambda n, t2} \end{pmatrix} \quad (3)$$

In the example mentioned before, the derived features Fλi,ti relate to intensities Iλi, ti. The feature vector F(Pi) is used together with the respective reference disease activity Aref(Pi) for each patient in order to find a regression vector R satisfying the following condition for all patients P1, . . . , PK:

$$A(P_i) \to A^{ref}(P_i), \text{ with } A(P_i) = F(P_i) \cdot R \quad (4)$$

Thus, in words, a regression vector R has to be found, wherein an inner product of the regression vector R and the feature vector F(Pi) approaches or is approximately equal to the reference disease activity Aref (Pi) determined by conventional means for all patients Pi. The regression vector R can be automatically derived by applying standard regression tools to the data, such as a partial-least-square-discriminant-analysis computer model or the like. However, when using the derived regression vector R for determining the disease activity of a patient later on, this requires optical data being collected at the plurality of wavelengths used for determining the regression vector R. In order to reduce the amount of data to be collected and the amount of wavelengths (S340), wavelengths are selected, which contain a high amount of information. These wavelengths correspond to wavelengths, at which the regression vector R has a large absolute amplitude, i.e. at which extrema in the spectrum of the regression vector R are located, since these represent the signal of interest or compensate for interfering signals.

Figure 8:
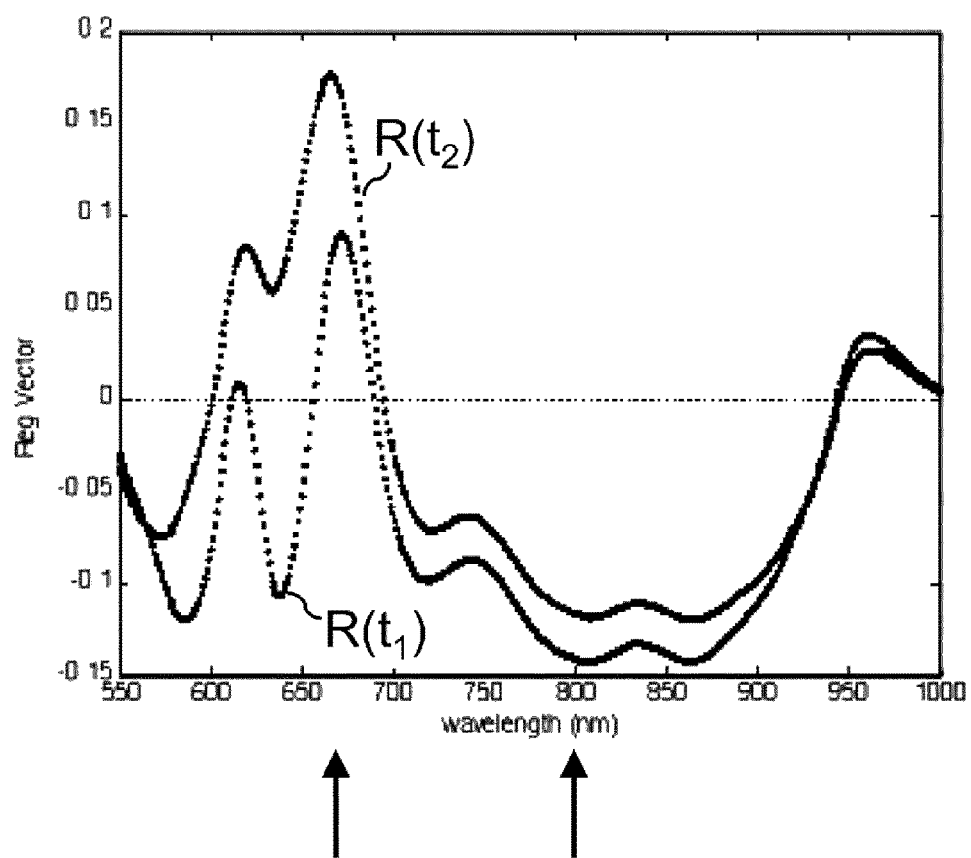
FIG. 8 illustrates a spectrum, wherein two regression vectors are plotted against wavelengths.

In FIG. 8, spectra of two regression vectors R(t1) and R(t2) are illustrated. In this example, two different time points t1 and t2 are selected, e.g. corresponding to the time before and after inflation of the pressure cuff 100, respectively. Then, corresponding regression vectors R(t1) and R(t2) are determined and plotted versus the wavelengths used in the optical measurements. From this spectrum, six wavelengths that comprise a high amount of information are exemplarily selected, as illustrated in Table 2:

TABLE 2

| λ (nm) ± 10 nm | Regression vector |
|---|---|
| before inflation | R(t₁) |
| 586 | −0.514 |
| 638 | −3.084 |

TABLE 2-continued

| λ (nm) ± 10 nm | Regression vector |
|---|---|
| 666 | 2.590 |
| 808 | −9.399 |
| 835 | −8.494 |
| 864 | −8.956 |
| after inflation | R(t₂) |
| 586 | −0.746 |
| 638 | 0.915 |
| 666 | 5.850 |
| 808 | −7.876 |
| 835 | −7.173 |
| 864 | −7.651 |

The wavelengths in the tables are given with an accuracy of ±10 nm. Having selected these wavelengths $\lambda_1, \ldots, \lambda_6$, a new feature vector F(P$_i$) is generated for each patient, comprising only the transmission intensities at the selected wavelengths $\lambda_1, \ldots, \lambda_6$ and time points $t_1, t_2$. Then, the steps S330-350 are repeated, so that in the next iteration, four wavelengths $\lambda_1, \ldots, \lambda_4$ can be selected. An example for these wavelengths is illustrated in Table 3:

TABLE 3

| λ (nm) ± 10 nm | Regression vector |
|---|---|
| before inflation | R(t₁) |
| 666 | 6.362328589 |
| 808 | −68.64910992 |
| 835 | −26.60977835 |
| 864 | −17.61730505 |
| after inflation | R(t₂) |
| 666 | −1.662144001 |
| 808 | −4.118865457 |
| 835 | 29.64944373 |
| 864 | 36.8147824 |

The iterations of steps S330-S350 are repeated, until the desired number n* of wavelengths is reached. However, optical data derived at these n* wavelengths should still be sufficient to reliably and accurately determine a disease activity A (S360). Since it is advantageous with respect to costs and design effort to sequentially irradiate discrete wavelengths and to use a broadband monochrome detector for recording the transmission, preferably only two wavelengths λ1, λ2 are used after completed setup of the system. These wavelengths λ1, λ2 and the corresponding values of the regression vectors are illustrated in table 4 for time points t1 (before inflation) and t2 (after inflation):

TABLE 4

| λ (nm) ± 10 nm | Regression vector |
|---|---|
| before inflation | R(t₁) |
| 666 | −1.318393361 |
| 808 | −27.20621001 |
| after inflation | R(t₂) |
| 666 | 5.982552148 |
| 808 | −23.81493673 |

By means of this setup method, a few most significant wavelengths can be selected by using a regression vector using a set of known spectra coupled to known values for disease activity. Hence, the amount of data recorded in an examination process is reduced and the analysis is simplified and accelerated.

Moreover, as an alternative to the expression (1), the determined regression vector R may be used in later patient examinations for determining the disease activity, e.g. for the two wavelengths in table 4 according to equation (5):

$$A(P_i) = R \cdot F(P_i) \tag{5}$$

$$= \begin{pmatrix} -1.32 \\ -27.2 \\ 5.98 \\ -23.8 \end{pmatrix} \cdot \begin{pmatrix} I(666 \text{ nm}, t_1) \\ I(808 \text{ nm}, t_1) \\ I(666 \text{ nm}, t_2) \\ I(808 \text{ nm}, t_2) \end{pmatrix}$$

$$= -1.32^* \begin{pmatrix} \text{transmission intensity at ca.} \\ 660 \pm 10 \text{ nm before inflation} \end{pmatrix} -$$

$$27.2^* \begin{pmatrix} \text{transmission intensity at ca.} \\ 808 \pm 10 \text{ nm before inflation} \end{pmatrix} +$$

$$5.98^* \begin{pmatrix} \text{transmission intensity at ca.} \\ 666 \pm 10 \text{ nm after inflation} \end{pmatrix} -$$

$$23.8^* \begin{pmatrix} \text{transmission intensity at ca.} \\ 808 \pm 10 \text{ nm after inflation} \end{pmatrix}.$$

Therefore, diagnostics of the disease activity can be performed by measuring the transmission of a joint or other area of interest 10 at two wavelengths and to time points in a perfusion variation cycle.

A lower cost can be realized by using only a single wavelength. For example, the wavelength could be selected to be 808±10 nm or 666±10 nm.

Thus, according to the present invention, a disease activity and a course of disease can be determined in a very accurate and reliable manner, without requiring complex and costly examination in terms of labor and time. Moreover, a doctor is provided with a single value indicating the disease activity, which he can consider when deriving a diagnosis among other inputs, such as patient history, other diseases, risks of side effects etc. Thus, treatment decisions and workflow efficiency are improved. Since the determination of the disease activity is performed based on optical data, only optical measurements are required. This is convenient for the patient as well as for the doctor, because the optical measurements can be easily performed in a medical practice without pain or discomfort.

It will be appreciated that the invention also applies to computer programs, particularly computer programs on or in a carrier, adapted to put the invention into practice.

Such a computer program may, for example, comprise instructions for causing a processor system to perform the steps of deriving features from detected intensities of light under at least two different perfusion conditions in an area of interest. and determining the disease activity using these features, in the way set forth herein. The program may be in the form of a source code, an object code, a code intermediate source and an object code such as in a partially compiled form, or in any other form suitable for use in the implementation of the method according to the invention.

It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions).

Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method. Functional units described herein may also be implemented by means of hardware entities, such as dedicated electronic circuits.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

What is claimed is:

1. A system for determining a disease activity of arthritis with respect to an area of interest of a body, the system comprising:
    a perfusion manipulator adapted to vary a blood perfusion in the area of interest, wherein the area of interest includes a joint;
    an irradiation unit adapted to irradiate the area of interest with light; and a detection unit adapted to detect intensities of light reflected and/or transmitted by the area of interest under at least two different perfusion conditions in the area of interest; and a controller adapted to:

record an intensity curve of detected intensities of light over time;

derive features from the detected intensities of light by fitting at least a part of the intensity curve by a fit function having fit parameters and using at least some of the fit parameters as the features for determining the disease activity; and determine the disease activity of arthritis as a single value or a scalar value based on the features by using a predetermined regression vector, wherein the controller is adapted to derive the features from the detected intensities of at least one predetermined wavelength or at least two predetermined wavelengths;

wherein the controller is adapted to determine the disease activity using an inner product of the regression vector and a feature vector; and wherein the feature vector comprises at least the features derived from the intensity curve of the predetermined wavelength or intensity curves of the at least two predetermined wavelengths.

2. The system of claim 1, wherein the irradiation unit is adapted to irradiate the area of interest with light of at least one wavelength or at least two wavelengths.

3. The system of claim 2, wherein the irradiation unit is adapted to sequentially irradiate the area of interest with the at least two predetermined wavelengths.

4. The system of claim 1, wherein the detection unit is adapted to differentiate between different wavelengths.

5. The system of claim 1, wherein the perfusion manipulator is adapted to cyclically vary the blood perfusion in the area of interest.

6. The system of claim 1, wherein said at least one predetermined wavelength or at least two predetermined wavelengths correspond to a wavelength or wavelengths that are determined to be the most significant wavelengths for determining the disease activity.

7. The system of claim 1, wherein the wavelength or wavelengths include:

one wavelength of ca. 666±10 nm.

8. The system of claim 1, wherein the features derived from the detected intensities of light include at least one of a maximum intensity, a minimum intensity, a drift, an intensity amplitude, a drop time, and an inflection point, or any combination thereof.

9. The system of claim 1, wherein the detected intensities of light relate to optical measurements performed for more than one area of interest, and the controller is adapted to derive the features from the detected intensities of light for each area of interest.

10. The system of claim 1, wherein the controller is adapted to:

determine at least one regression vector indicative for the disease activity by analyzing intensities measured for a plurality of patients having different levels of disease activity at a plurality of different wavelengths; and select the at least two predetermined wavelengths corresponding to extrema in a spectrum of the regression vector.

11. The system of claim 1, wherein the wavelength or wavelengths include two wavelengths of ca. 666±10 nm and 808±10 nm.

12. The system of claim 1, wherein the wavelength or wavelengths include four wavelengths of ca. 666±10 nm, 808±10 nm, 835±10 nm, and 864±10 nm.

13. The system of claim 1, wherein the wavelength or wavelengths include six wavelengths of ca. 586±10 nm, 638±10 nm, 666±10 nm, 808±10 nm, 835±10 nm, and 864±10 nm.

14. A method for determining a disease activity with respect to an area of interest in a body, the method comprising:

varying a blood perfusion in the area of interest wherein the area of interest includes a joint;

irradiating the area of interest with light; and detecting intensities of light reflected and/or transmitted by the area of interest under at least two different perfusion conditions in the area of interest;

recording an intensity curve of detected intensities of light over time;

deriving features from the detected intensities of light by fitting at least a part of the intensity curve by a fit function having fit parameters and using at least some of the fit parameters as the features for determining the disease activity;

deriving the features from the detected intensities of at least one predetermined wavelength or at least two predetermined wavelengths; and determining the disease activity of arthritis as a single value or a scalar value based on the features by using an inner product of a predetermined regression vector and a feature vector wherein the feature vector comprises at least the features derived from the intensity curve of the predetermined wavelength or intensity curves of the at least two predetermined wavelengths.

15. The method of claim 14, wherein irradiating the area of interest with light comprises irradiating the area of interest with light of at least one wavelength or at least two wavelengths.

16. The method of claim 14, wherein the wavelength or wavelengths include two wavelengths of ca. 666±10 nm and 808±10 nm.

17. The method of claim 14, wherein the wavelength or wavelengths include four wavelengths of ca. 666±10 nm, 808±10 nm, 835±10 nm, and 864±10 nm.

18. The method of claim 14, wherein the wavelength or wavelengths include six wavelengths of ca. 586±10 nm, 638±10 nm, 666±10 nm, 808±10 nm, 835±10 nm, and 864±10 nm.

* * * * *